US012797239B2

(12) United States Patent
Tumlinson

(10) Patent No.: US 12,797,239 B2
(45) Date of Patent: Nov. 17, 2026

(54) LOW DEAD VOLUME VITREOUS SAMPLING AND DRUG DELIVERY DEVICE

(71) Applicant: Verily Health Inc., Dallas, TX (US)

(72) Inventor: Alexandre R. Tumlinson, South San Francisco, CA (US)

(73) Assignee: Verily Health Inc., Dallas, TX (US)

( * ) Notice: Subject to any disclaimer, the term of this patent is extended or adjusted under 35 U.S.C. 154(b) by 670 days.

(21) Appl. No.: 18/122,890

(22) Filed: Mar. 17, 2023

(65) Prior Publication Data

US 2024/0307221 A1 Sep. 19, 2024

(51) Int. Cl.

| | |
|---|---|
| ***A61F 9/007*** | (2006.01) |
| ***A61F 9/00*** | (2006.01) |
| *A61M 37/00* | (2006.01) |

(52) U.S. Cl.

CPC ........ *A61F 9/00745* (2013.01); *A61F 9/0008* (2013.01); *A61F 9/0026* (2013.01); *A61F 9/00736* (2013.01); *A61M 37/0092* (2013.01)

(58) Field of Classification Search

CPC ............ A61B 10/0045; A61B 10/0096; A61B 10/0283; A61B 10/026; A61B 10/0233; A61M 2210/0612; A61M 5/19; A61M 5/3146; A61M 37/0092; A61J 1/2096; A61F 9/00745; A61F 9/00781; A61F 9/00736; A61F 9/0008; A61F 9/0026

See application file for complete search history.

(56) References Cited

U.S. PATENT DOCUMENTS 11,020,270 B1 * 6/2021 Peyman .............. A61F 9/00763
11,806,277 B2 * 11/2023 Tumlinson .......... A61F 9/00736
2013/0178789 A1 * 7/2013 Mackool ................ A61B 90/37 604/22
2021/0353455 A1 11/2021 Tumlinson
2022/0370293 A1 * 11/2022 Tumlinson ......... A61B 10/0045
2024/0050274 A1 * 2/2024 Tumlinson .......... A61F 9/00736
2024/0307040 A1 * 9/2024 Tumlinson ......... A61B 10/0045
2025/0041116 A1 * 2/2025 Jia ....................... A61F 9/00736

FOREIGN PATENT DOCUMENTS

WO WO-2011154971 A1 * 12/2011 ......... A61F 9/00745
WO 2019018367 A1 1/2019

OTHER PUBLICATIONS

International Searching Authority, International Search Report and Written Opinion of the International Searching Authority, PCT/US2023/015460, mailed Nov. 13, 2023, European Patent Office, Netherlands, 15 pages.

* cited by examiner

*Primary Examiner* — Stephanie Sebasco Cheng
(74) *Attorney, Agent, or Firm* — Christensen O'Connor Johnson Kindness PLLC

(57) ABSTRACT

A device for removing vitreous from an eye includes a needle defining a lumen and a port extending to the lumen. The needle is configured for insertion into the vitreous of the eye. A sample container is coupled to the needle and includes a chamber in fluid communication with the lumen. A mechanism is provided for inducing vibration in the needle to draw a sample of the vitreous into the port and to the chamber. A drug delivery system is provided for delivering a therapeutic agent through the port. At least one of the sample container and the drug delivery system extends into the vibration inducing mechanism for reducing an overall length of the device.

21 Claims, 8 Drawing Sheets

LOW DEAD VOLUME VITREOUS SAMPLING AND DRUG DELIVERY DEVICE

TECHNICAL FIELD

The subject matter described herein relates to devices, systems, and methods for injection of substances into, and sampling of, aqueous and vitreous humors of the eye. The disclosed intravitreal injection and sampling device has particular but not exclusive utility for diagnosis and treatment of ophthalmic disorders in humans.

BACKGROUND

Vitreous humor is a colorless, gelatinous fluid within an eye or eyeball of humans or other vertebrates composed of approximately 98-99% water with trace amounts of hyaluronic acid, glucose, anions, cations, ions, and a fine network of collagen. Vitreous humor provides support to the surrounding structures of the eye, absorbs mechanical trauma, and provides circulation and regulation of oxygen, metabolites and nutrients. It is produced largely by cells of the ciliary body. Changes in vitreous structure that occur with aging, are important in the pathogenesis of many vitreoretinal diseases.

Intraocular pressure (IOP) quantifies the pressure of the vitreous humor inside the eye. Many individuals suffer from disorders, such as glaucoma, that are associated with chronic heightened IOP. Over time, heightened IOP can cause damage to the optical nerve of the eye, leading to loss of vision.

Presently, treatment of ophthalmic disorders mainly involves periodically administering pharmaceutical agents to the eye. These drugs can be delivered by, for example, intravitreal injection. Intravitreal injection is one of the most common surgical procedures performed in ophthalmology today. A variety of drugs are delivered directly to the clear vitreous gel that supports the globe of the eye. These drugs act directly in the vitreous or in the surrounding retinal tissues over the following months. For example, intravitreal injection is a common route of delivery for vascular endothelial growth factor inhibiting (anti-VEGF) proteins, which are highly potent compounds tolerated at high doses, with intravitreal half-lives about one week. Anti-VEGF biologics and steroids are the most commonly administered drugs by this route. These drugs may be administered on a chronic basis.

One recommended procedure for intravitreal injection includes preparation of an injection needle, topical anesthesia and disinfection of the eye surface, holding the eye open with a lid speculum or other means, optional lateral dislocation of the conjunctiva at the injection site, and insertion of the needle a few mm lateral to the limbus to approximately the full depth of the needle, injecting the drug, withdrawing the needle, and allowing the conjunctiva to cover the injection site. Post injection care typically includes a basic verification of functional vision such as requesting the patient to count the number of fingers shown by the doctor. This functional test verifies that acute IOP increase due to injection has not impacted the optic nerve head in a way that requires immediate relief.

Another important ophthalmic procedure is vitreous sampling. Vitreous sampling may inform various aspects of eye care. Samples of vitreous may be analyzed for cellular content and extracellular structure by histology or immunologic analysis. Histology can, for example, provide a definitive diagnosis for the type of infection causing endophthalmitis.

Identification of the type of immune cells present and the immune mediator proteins expressed may inform the treatment of uveitis. Identification of the amount of VEGF present in the vitreous may give an indication of how likely imminent neovascularization is to occur or how likely it is that VEGF compounds are responsible for an observed case of neovascularization. Non-responders to anti-VEGF treatment remains one of the most troublesome aspects of treating neovascularization in exudative, age-related vascular degeneration (also known as wet AMD) and diabetic retinopathy.

Two common methods of vitreous sampling—with a cutter or with needle aspiration—appear to be approximately equivalent for the purposes of protein analysis. A state of the art miniature cutting tool may be delivered through a 23-gauge trocar. Needle aspiration may be performed with needles as small as 30-gauge (about half the diameter of 23 gauge). Fine gauge may increase the probability of a dry tap and/or change the properties of the aspirated material by acting as a filter. Small gauge may have an advantage in that traction may not be introduced on the gel matrix because the gel matrix cannot be pulled into the small needle bore. Vitreous samples are typically frozen or otherwise stabilized so that they can be processed in a laboratory outside of the operating room or ophthalmic office setting.

Injection of therapeutic doses of medication into the vitreous or aqueous humor inside the eye can increase IOP by as much as 25 mmHg, which is substantially greater than threshold levels that are considered potentially harmful. Evidence shows that while such IOP increases are transient, they are in fact associated with an iatrogenic glaucoma resulting in measurable loss of nerve fiber layer and visual function over a course of only several treatments in patients with 'normal' resting IOP. See Saxena, S., Lai, T. Y., Koizumi, H. et al., "Anterior chamber paracentesis during intravitreal injections in observational trials: effectiveness and safety and effects," International Journal of Retina and Vitreous, 5, 8 (2019). Therefore, it is sometimes desirable to remove a small volume of humor (whether aqueous, vitreous or both) from the eye before injecting a comparable volume of medication. However, removal of a volume of humor may result in insufficient pressure, which can also be harmful to the eye.

Therefore, in the case of diagnostic sampling of humors, it may be necessary or beneficial to inject a volume of fluid (whether medicated or otherwise) to replace the withdrawn humors. In either case, care must be taken to ensure that the removed and injected volumes are comparable, and in either case, two separate procedures (a sampling procedure and an injection procedure) are typically required.

When ultrasonic or hypersonic means are used to help retrieve the vitreous humor sample, the sum length of the resonant assembly is usually an integer number of quarter wavelengths, given the speed of sound in the material. To this end, the piezo crystals are typically located at a displacement node in the material and the horn and back mass are approximately one quarter wavelength in axial length. With this in mind, it is desirable to limit the overall length of the vitrectomy device and/or limit the dead volume therein-both of which can also contribute to making the device unwieldly in a user's hand.

SUMMARY

In one example, a device for removing vitreous from an eye includes a needle defining a lumen and a port extending to the lumen. The needle is configured for insertion into the vitreous of the eye. A sample container is coupled to the needle and includes a chamber in fluid communication with the lumen. A mechanism is provided for inducing vibration in the needle to draw a sample of the vitreous into the port and to the chamber. A drug delivery system is provided for delivering a therapeutic agent through the port. At least one of the sample container and the drug delivery system extends into the vibration inducing mechanism for reducing an overall length of the device.

In another example, a device for removing vitreous from an eye includes a needle defining a lumen and a port extending to the lumen. The needle is configured for insertion into the vitreous of the eye. A sample container is coupled to the needle and includes a chamber. A conduit fluidly connects the lumen and the chamber such that the needle and the sample container are longitudinally misaligned from one another. A mechanism induces vibration in the needle to draw a sample of the vitreous into the port and to the chamber. A drug delivery system delivers a therapeutic agent through the port.

In another aspect of the invention, the mechanism, the container, and the drug delivery system are longitudinally aligned with one another.

In another aspect of the invention, taken alone or in combination with any other aspect, the mechanism is an ultrasonic transducer having a back mass.

In another aspect of the invention, taken alone or in combination with any other aspect, the sample container extends into a pocket in the back mass.

In another aspect of the invention, taken alone or in combination with any other aspect, the sample container and the drug delivery system extend into a pocket in the back mass.

In another aspect of the invention, taken alone or in combination with any other aspect, the ultrasonic transducer is a langevin transducer.

In another aspect of the invention, taken alone or in combination with any other aspect, the ultrasonic transducer operates at a frequency of about 20 kHz to about 50 KHz.

In another aspect of the invention, taken alone or in combination with any other aspect, the ultrasonic transducer energizes piezoelectric crystals to cause an acoustic horn to vibrate.

In another aspect of the invention, taken alone or in combination with any other aspect, a distal end of the needle has a sharpened tip configured for insertion into or through at least one of a sclera, a pars plana or a vitreous body of the eye.

In another aspect of the invention, taken alone or in combination with any other aspect, a controller is configured to control the mechanism for stopping and starting vibration of the needle.

In another aspect of the invention, taken alone or in combination with any other aspect, the port, in combination with the vibrating needle, is configured to liquefy the vitreous by disrupting the integrity of the vitreous gel using at least one of shear force or viscous heat.

In another aspect of the invention, taken alone or in combination with any other aspect, the mechanism has a laterally extending passage for receiving an end of the conduit.

In another aspect of the invention, taken alone or in combination with any other aspect, the back mass has a longitudinally extending passage aligned with the needle and receiving an end of the conduit.

Other objects and advantages and a fuller understanding of the invention will be had from the following detailed description and the accompanying drawings.

DETAILED DESCRIPTION

The subject matter described herein relates to devices, systems, and methods for injection of substances into, and sampling of, aqueous and vitreous humors of the eye. The disclosed intravitreal injection and sampling device has particular but not exclusive utility for diagnosis and treatment of ophthalmic disorders in humans.

Figure 1:
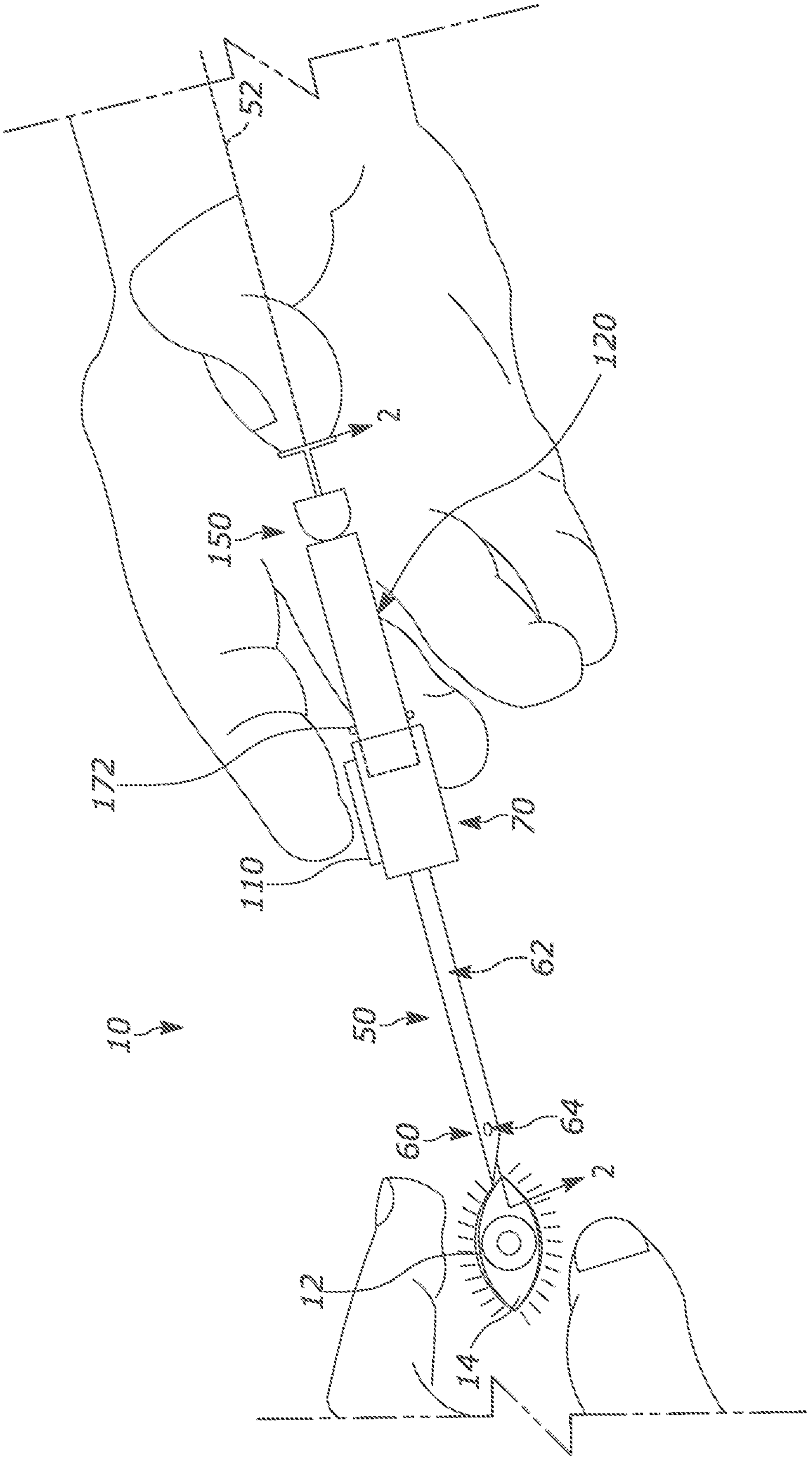
FIG. 1 is a schematic illustration of an example combined biological sampling and injection device in accordance with the present invention.

FIG. 1 illustrates an example combined biological sampling and injection assembly or device 10 in accordance with the present invention. The device 10 is operable by a user, e.g., a physician, to obtain a sample of vitreous humor 14 from an eye 12 of a patient.

Figure 2:
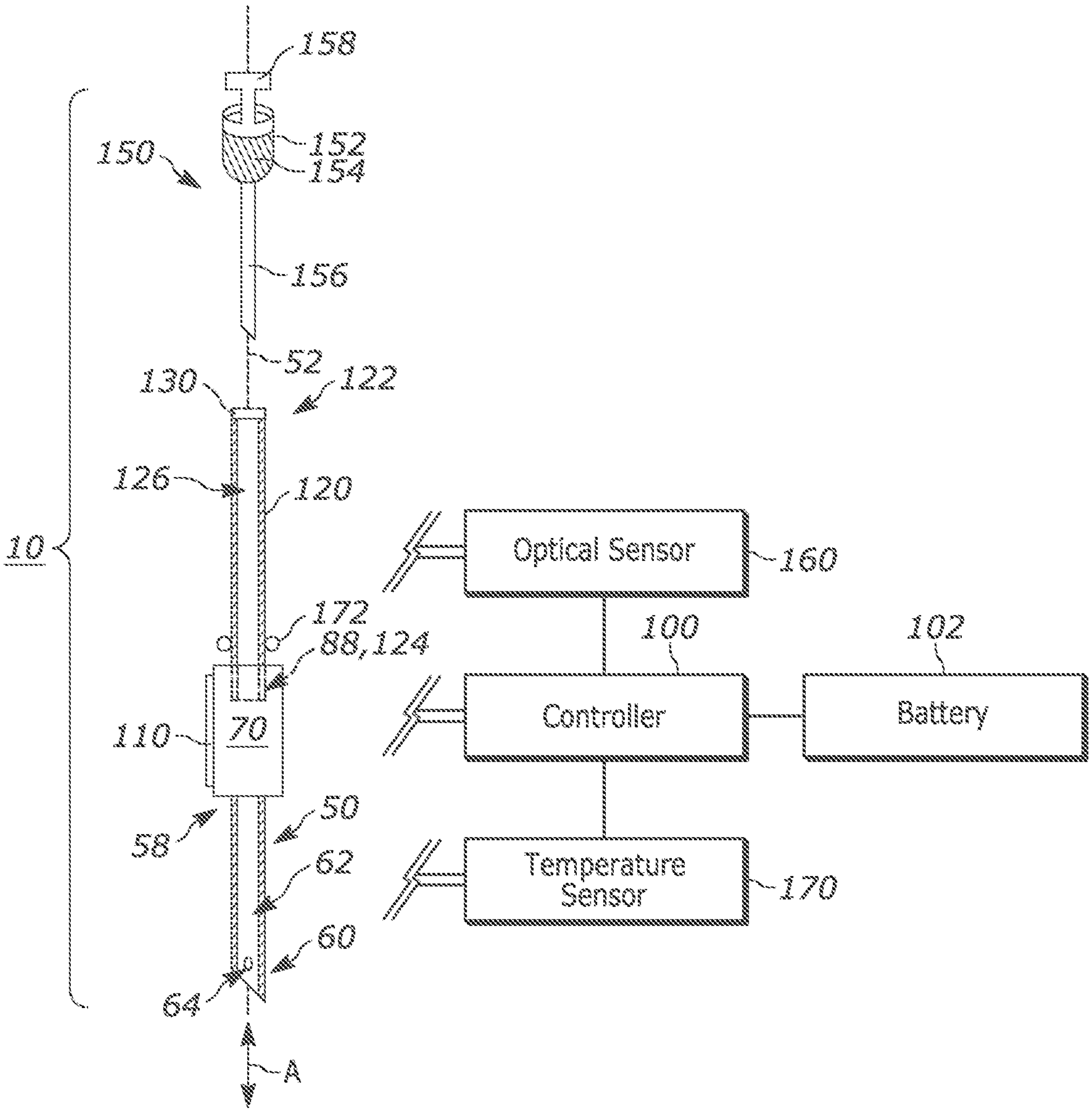
FIG. 2 is a section view of the device of FIG. 1 taken along line 2-2.

Referring to FIG. 2, the device 10 includes a tubular eye penetration member or needle 50 extending longitudinally along a centerline 52 from a proximal end 58 to a distal end 60. Each end 58, 60 can have a pointed, angled configuration or a blunt/rounded configuration. A lumen 62 extends between the ends 58, 60 along the length of the needle 50. At least one port 64 extends radially from the periphery of the needle 50 radially inward to the lumen 62. It will be appreciated, however, that the port 64 could alternatively or additionally extend longitudinally through the distal end 60 of the needle 50. In other words, the port 64 can be coextensive with the lumen 62 (not shown).

A pressure modulation system or mechanism 70 is provided for modulating the pressure of any fluid delivered to or provided within the lumen 62 and/or modulating movement of the needle 50. In one example, the pressure modulation system 70 includes a hollow vibration source, such as an ultrasonic transducer. In particular, the ultrasonic transducer can constitute a langevin transducer.

Figure 3A:
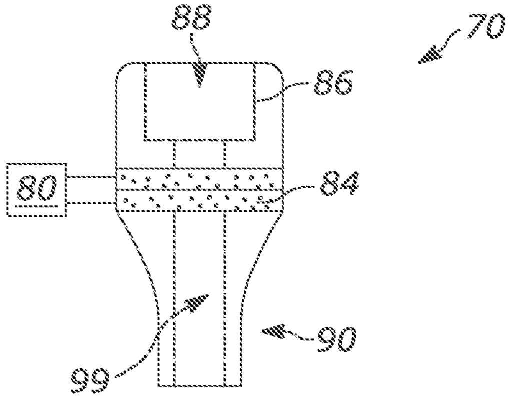
FIG. 3A is a schematic illustration of an example pressure modulation system of the device.
Figure 3B:
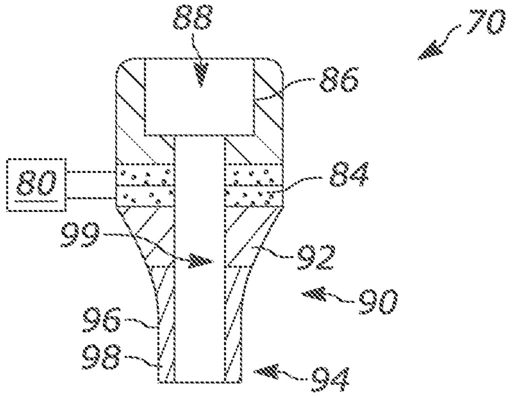
FIG. 3B is a section view of the pressure modulation system of FIG. 3A.

FIGS. 3A-3B illustrate the pressure modulation system 70 in more detail. The transducer 80 can be configured to drive an axial vibration of the needle 50 such that the needle tip displacement (stroke length) is on the order of about 5-100 μm at a frequency of about 20 kHz to about 50 kHz. With this in mind, the transducer 80 is coupled to piezoelectric crystals 84 for energizing the same upon activation of an actuator 110 provided along the device 10 (see FIG. 1).

A back mass 86 cooperates with the energized piezoelectric crystals 84 to vibrate an acoustic horn 90 connected to the needle 50. In one example, a pocket or recess 88 is formed in the proximal end (as shown) of the back mass 86 and extends towards the piezoelectric crystals 84.

The horn 90 can be solid and/or fluid in construction. In one instance shown in FIG. 3B, the horn 90 includes a solid portion 92 and a liquid portion 94. Both portions 92, 94 in this construction are cylindrical/hollow to accommodate the needle 50. The solid portion 92 is secured/connected to the back mass 86. The liquid portion 94 extends distally away from the solid portion 92 and towards the port(s) 64. The liquid portion 94 can include a tube 96 and a liquid 98, e.g., an aqueous liquid, disposed therein. The longitudinal cross-section of the horn 90 decreases in a direction extending from the back mass 86 towards the distal end 60 of the needle 50. Regardless of the exact configuration of the horn 90, a passage 99 extends longitudinally from the pocket 88 to the distal extent of the horn 90.

Returning to FIG. 2, the pressure modulation system 70—including the actuator 110—is powered by a battery 102 coupled to the needle 50. The actuator 110 is also connected to a controller 100 such that controller controls activation/deactivation of the transducer 80 in response to user interaction with the actuator. In one example, pressing the actuator 110 causes the transducer 80 to apply ultrasonic pressure to the needle 50 such that the entire needle 50 axially vibrates in the manner indicated generally at A.

The device 10 further includes a sample container 120 for connection to the needle 50 to receive a sample of vitreous humor 14 from the eye 12. The sample container 120 is a hollow tube extending from a proximal end 122 to a distal end 124 and defining a central passage or chamber 126. The sample container 120 can be formed from a polymer and be solid, opaque or transparent.

Structure (illustrated schematically at 130) is provided at or over the proximal end 122 for sealing the proximal end of the chamber 126 in a desired manner. A sealing actuator 172, e.g., a pinching member, is provided around the distal end 124 for sealing the same. The chamber 126 is can be actively or passively sealed by the elements 130, 172 to have a predetermined pressure, e.g., below, at or above atmospheric pressure. To this end, the structure 130 can be formed as a hydrophobic barrier or septum that enables the free exchange of gas between the atmosphere and the chamber 126 but prevents liquid from exiting the chamber. Alternatively or additionally, the structure 130 can include a check valve or other conventional sealing structure.

The device 10 can further include a drug delivery system or syringe 150 for delivering medication to the eye 12 following removal of vitreous humor 14. The drug syringe 150 includes a hollow container 152 for holding a drug 154 of known medication, therapeutic agent, etc. The drug 154 can be in a vial, in liquid form, etc. A needle 156 extends into the container 152 and is in fluid communication with the drug 154. A plunger 158 cooperates with the container 152 to selectively expel the drug 154 out of the container 152 and through the needle 156 in a known manner.

When the device 10 is assembled, the proximal end 122 of the sample container 120 is received in the pocket 88 of the back mass 86, i.e., the sample container and back mass are at least partially nested with one another. In any case, this places the lumen 62 and the chamber 126 in fluid communication with one another and places the chamber 126 axially between the proximal end 58 of the needle 50 and the sealing structure 130. The sealing actuator 172 can be positioned outside the pocket 88 (as shown) or within the pocket (not shown). In any case, the sample container 120 is longitudinally aligned with the needle 50 along the centerline 52. The device 10 is therefore substantially longitudinally symmetric.

Figure 4:
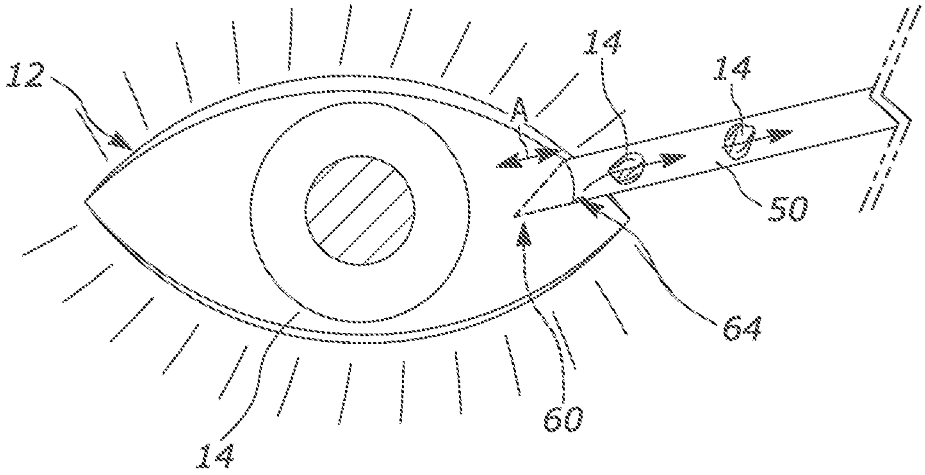
FIG. 4 is an enlarged view of vitreous sampling with the device.

In operation and referring further to FIG. 4, the distal end 60 of the needle 50 is positioned adjacent the eye 12 and inserted therein. Once the distal end 60 is positioned within the vitreous humor 14, the pressure modulation system 70 is activated by the user (via the actuator) or automatically activated (in response to sensor readings). In either case, forces are imparted on the vitreous humor 14, including shear and viscous heating, that act to disrupt the integrity of the vitreous humor. More specifically, the pressure modulation system 70—by axially vibrating the distal end 60 of the needle 50 in the manner A-breaks apart and liquefies the vitreous humor 14 sufficient to draw portions of the vitreous humor into the radial port(s) 64. The vitreous humor 14 passes radially inward through the port(s) 64 and into the lumen 62 of the needle 50, ultimately passing through the needle, through the passage 99 in the pressure modulation system 70, and into the chamber 126.

Referring further to FIG. 2, an optical sensor 160 can be positioned on the container 120 and has a probe wavelength transmissive to the chamber 126 walls but opaque to the entering vitreous humor 14 sample. The optical sensor 160 measures the volume of the sample received by the chamber 126 via optical absorption and sends signals indicative thereof to the controller 100. Alternatively or additionally, a temperature sensor 170 can be connected to the controller 100 and used to monitor the level of vitreous sample within the chamber 126 by measuring temperature changes in the chamber. Alternatively or additionally, a pressure sensor (not shown) can be connected to the controller 100 and used to monitor the level of vitreous sample within the chamber 126 by measuring pressure changes in the chamber.

Once the chamber 126 is full, the system times out or the user aborts the sampling procedure, the controller 150 can deactivate the pressure modulation system 70 and thereby cease vibration of the needle 50. Regardless, the sealing actuator 172 located adjacent the distal end 124 of the sampling container 120 is then actuated to pinch or close off the sampling container and thereby retain/seal the sample of vitreous humor 14 within the chamber 126.

Figure 5A:
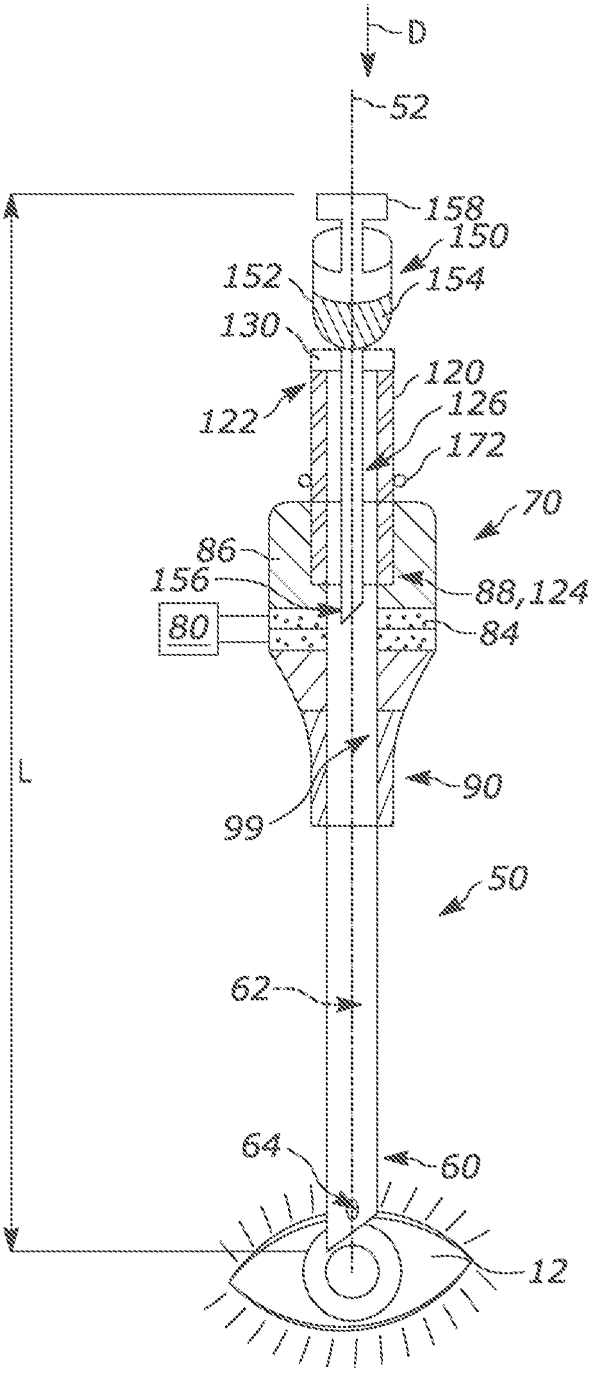
FIG. 5A is a schematic illustration of a first example coupling between a sample container and the pressure modulation system.

Referring to FIG. 5A, while the needle 50 remains within the eye 12, the syringe 150 is aligned with the chamber 126 of the sample container 120. The needle 156 is advanced in the direction D until it pierces and passes through both the sealing structure 130 and the sealing actuator 172 and enters the passage 99. In other words, the needle 156 passes through the chamber 126 with the sample of vitreous humor 14 therein. This places the needle 156 in fluid communication with the passage 99 and, thus, in fluid communication with the lumen 62 and radial port(s) 64. That said, thereafter depressing the plunger 158 in the direction D pushes the drug 154 out of the container 152, through the needle 156, into the lumen 62 of the needle 50, and out of the device 10 through the radial port(s) 64 to be fully injected into the eye 12 where the vitreous humor 14 sample was removed. After the drug 154 is delivered, the entire device 10 can be retracted out of the eye 12 by pulling the same in the direction opposite the direction D.

Figure 5B:
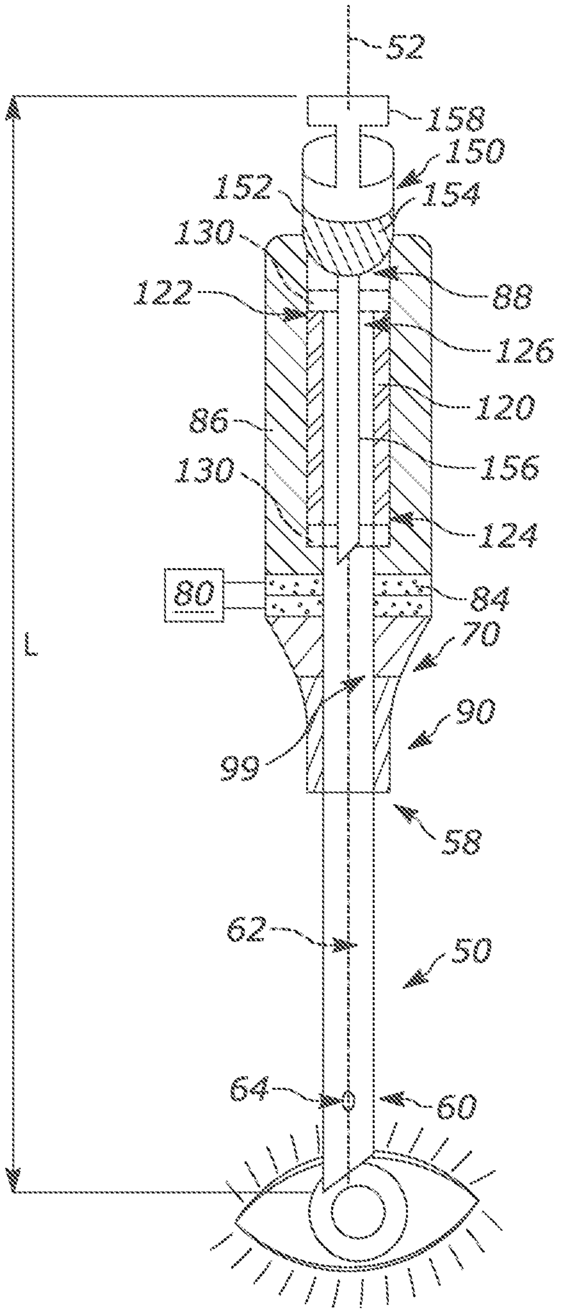
FIG. 5B is a schematic illustration of a second example coupling between the sample container and the pressure modulation system.

In another example shown in FIG. 5B, the length of the back mass 66 as well as the size of the pocket 88 therein are configured to receive portions of both the sample container 120 as well as the drug delivery system 150. In one example, the pocket 88 receives the entire sample container 120 and the container 152 of the drug delivery system 150 extends into pocket 88. Consequently, the pressure modulation system 70, sample container 120, and drug delivery system 150 are all nested with one another and longitudinally aligned with one another along the centerline 52. The device 10 is therefore substantially longitudinally symmetric.

In either case, the configuration of the device 10 is advantageous because nesting at least one of the sample container 120 and the drug delivery system 70 within the pressure modulation system 70 (more specifically within the back mass 86) reduces the overall length, indicated at L, of the device. Consequently, the configuration of the device 10 reduces the dead volume thereof and helps maximize the size of the chamber 126 that can be used. The volume of vitreous humor 14 sample that can be collected can therefore be maximized. Furthermore, the more compact device 10 configuration helps to improve hand ergonomics for the user and make shipping and storage of the device more efficient.

Figure 6:
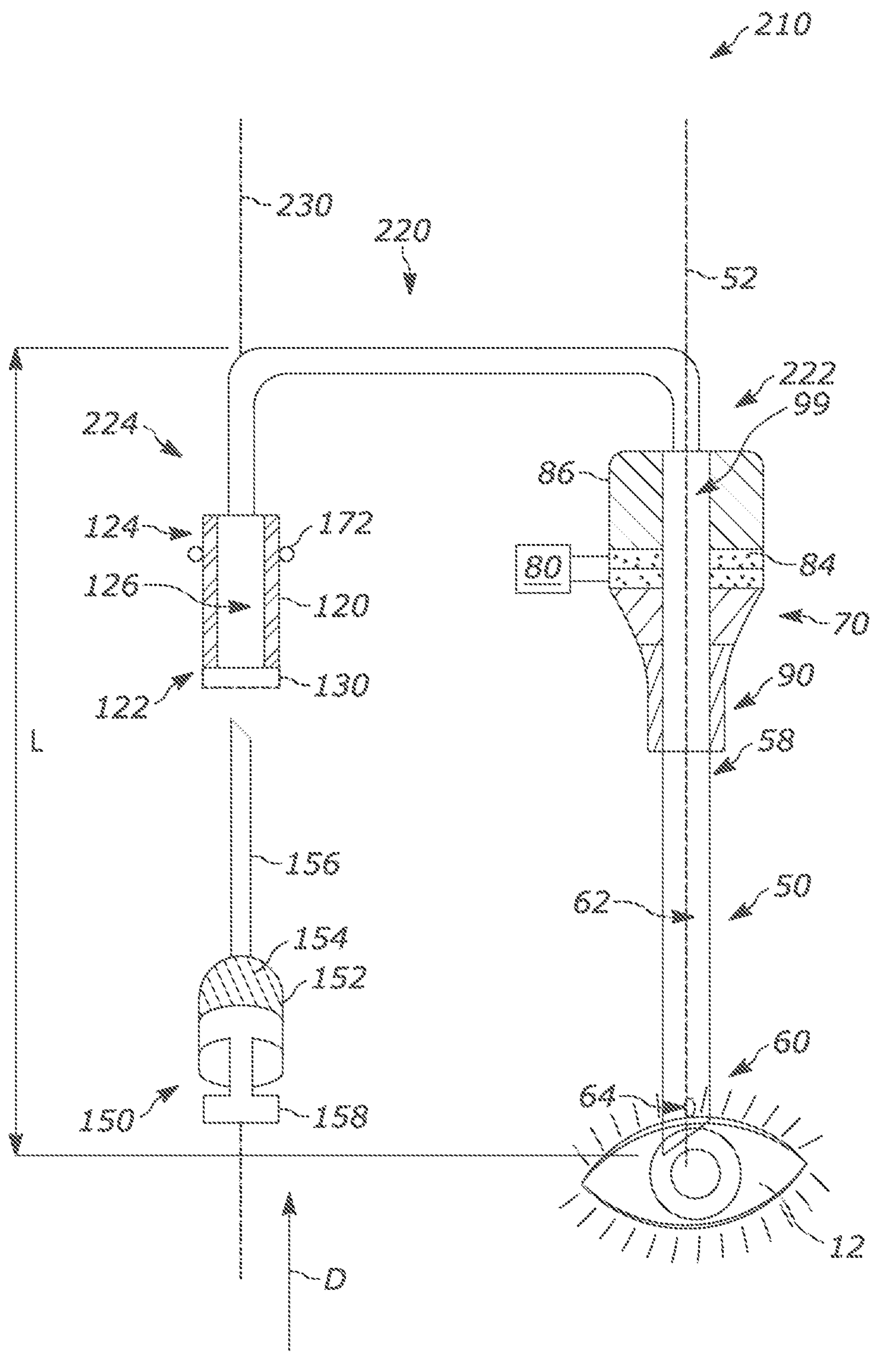
FIG. 6 is a schematic illustration of another example sampling and injection device.

FIG. 6 illustrates another example device 210 in accordance with the present invention. Features in FIG. 6 that are similar to those in FIG. 2 carry the same reference numbers. In FIG. 6, a conduit or tube 220 helps to fluidly connect the chamber 126 to the lumen 62. The conduit 220 can be made of a flexible material (such as rubber or the like) or a rigid material (such as steel microtubing or the like). In any case, the conduit 220 extends from a first end 222 connected to the back mass 86 to a second end 224 connected to the distal end 124 of the sample container 120. In this manner, the first end 222 is fluidly connected to the central passage 99 and, thus, fluidly connected to the lumen 62 of the needle 50. The second end 224 is fluidly connected to the chamber 126 of the sample container 120.

Regardless of the construction of the conduit 220, the device 210 is capable of being folded so as to greatly reduce its overall length L. More specifically, the flexible construction of the conduit 220 can be bent/curved away from the centerline 52 and extend backwards in a direction parallel to the centerline 52. The rigid construction of the conduit 220 can be pre-formed in the same bent/curved trajectory as the flexible construction. In both cases, the sample container 120 and drug delivery system 150 can be aligned along a second centerline 230 different, e.g., offset from or transverse to, the centerline 52. That said, neither the sample container 120 nor the drug delivery system 150 in this configuration help define or add to the length L of the device 210 because the sample container and drug delivery system are misaligned from the centerline 52.

Figure 7:
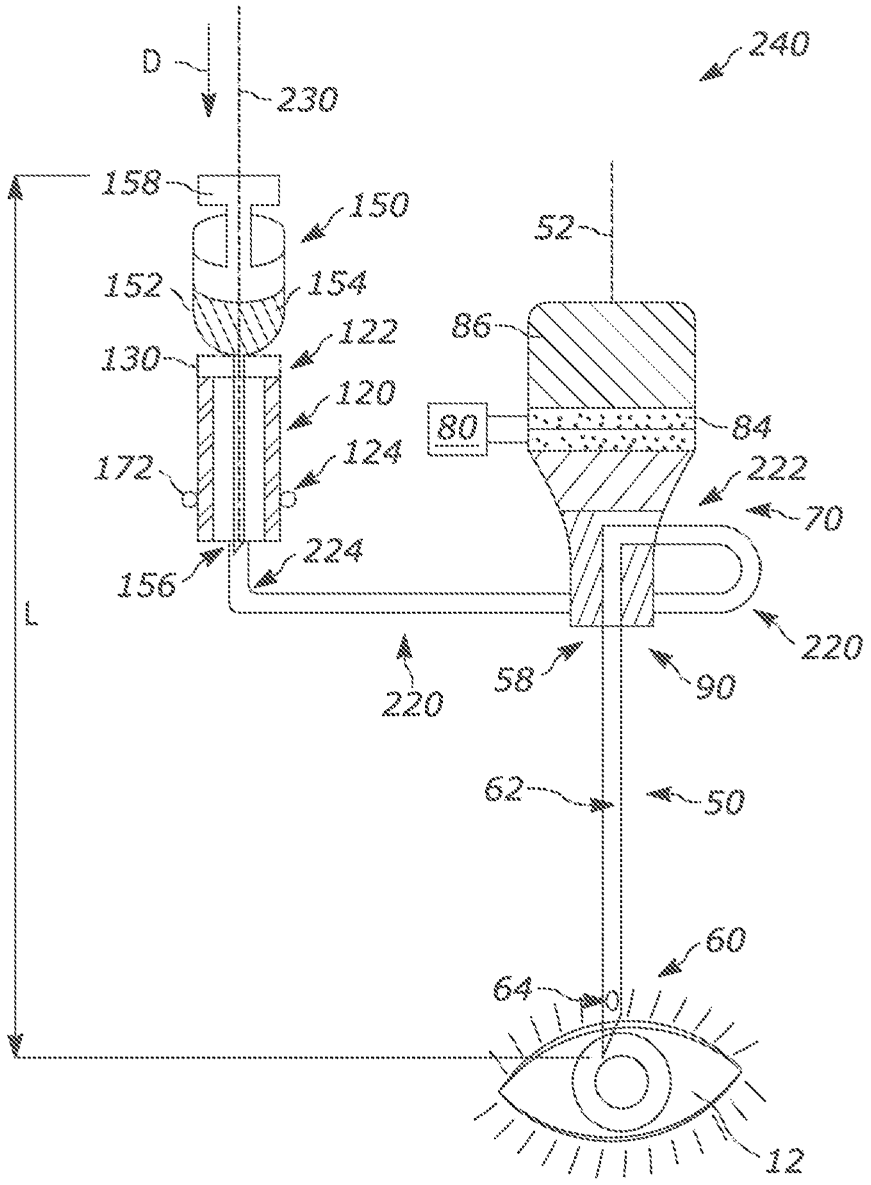
FIG. 7 is a schematic illustration of another example sampling and injection device.

In a similar, modified device 240 shown in FIG. 7, the conduit 220 extends laterally from the back mass 86 and connects to the sample container 120. The first end 222 of the conduit 220 can extend into the side of the horn 90 (as shown) or side of the back mass 86 (not shown). In either case, the passage 99 is substantially L-shaped and therefore extends along the centerline 52 before turning and extending laterally to the periphery of the back mass 86 or horn 90.

Regardless, the conduit 220—whether flexible or rigid—enables the sample container 120 and drug delivery system 150 to extend along the second centerline 230 to misalign the sample container and drug delivery system from the centerline 52. Depending on the length and/or trajectory of the conduit 220, the sample container 120 and the drug delivery system 150 may or may not contribute to the overall length L of the device 240. The length L of the device 240, however, is still less than if the sample container 120 and drug delivery system 150 were aligned with the needle 50 along the centerline 52.

It will be appreciated that having the conduit 220 extend laterally from the back mass 86 (or horn 90) necessarily introduces asymmetry into the pressure modulation system 70. Consequently, it may be beneficial to adjust the tuning of the vibration generated by the pressure modulation system 70 and/or add a balancing modification to the pressure modulation system, e.g., by making the passage 99 symmetric about the centerline 52. This could involve making the passage 99 T-shaped, in which case one end of the "T" would be connected to the first end 222 and the other end would be unconnected but would mitigate/eliminate the vibrational asymmetry.

It will be appreciated that additional, alternative configurations for the modulation mechanism can be implemented into the assemblies of the present invention. To this end, the modulation mechanisms can be mechanical-based and formed as a drill bit inside the needle or rely on oscillating guillotine blades driven by a variety of motor types.

The modulation mechanisms can be non-mechanical in nature. For instance, an energy delivery device can be provided on the distal end of the needle for helping to denature the vitreous gel in the eye. In one example, the energy delivery device includes one or more electrodes arranged circumferentially about the distal end of the needle and selectively energized by the controller. Furthermore, the electrodes can be arranged along the interior and/or exterior of the distal end of the needle.

Alternatively or additionally, one or more optical fibers can be provided on the distal end of the needle (along the interior and/or exterior thereof) for delivering a high energy pulse at a wavelength highly absorbed by water to locally disrupt the vitreous gel. The optical fibers can also be connected to and controlled by the controller.

Moreover, targeted Proteases such as collagenase, hyaluronidase, or others may be used to break down the specific proteins of the vitreous gel. These may be injected directly before the sampling or hours or weeks before sampling. Traditional chemicals such as strong acids or bases that are not particularly targeted may be injected alone or in combination with proteases to speed the chemical action to break down the structural proteins of vitreous.

The combined biological sampling and injection assemblies described herein are advantageous in that they provide for a small gauge, e.g., 30G or smaller, instrument that can directly penetrate the sclera, does not require protective measures for the sclera, does not require an external fluid source for the liquid column, and can be operated in a cordless manner. Furthermore, the assemblies provide multiple ways in which pressure modulation can be delivered to the liquid column at a manageable distance from the distal tip of the needle.

What have been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

What is claimed is:

1. A device for removing vitreous from an eye, comprising:

a needle defining a lumen and a port extending to the lumen, the needle being configured for insertion into the vitreous of the eye;

a sample container coupled to the needle and having a chamber in fluid communication with the lumen;

a vibration mechanism configured to induce vibration of the needle to draw a sample of the vitreous into the port and to the chamber; and a drug delivery system for delivering a therapeutic agent through the port, wherein at least one of the sample container and the drug delivery system extends into the vibration mechanism for reducing an overall length of the device.

2. The device recited in claim 1, wherein the mechanism, the container, and the drug delivery system are longitudinally aligned with one another.

3. The device recited in claim 1, wherein the mechanism comprises an ultrasonic transducer having a back mass.

4. The device recited in claim 3, wherein the sample container extends into a pocket in the back mass.

5. The device recited in claim 3, wherein the sample container and the drug delivery system extend into a pocket in the back mass.

6. The device recited in claim 3, wherein the ultrasonic transducer is a langevin transducer.

7. The device recited in claim 3, wherein the ultrasonic transducer operates at a frequency of 20 kHz to 50 kHz.

8. The device recited in claim 3, wherein the ultrasonic transducer energizes piezoelectric crystals to cause an acoustic horn to vibrate.

9. The device recited in claim 1, wherein a distal end of the needle comprises a sharpened tip configured for insertion into or through at least one of a sclera, a pars plana or a vitreous body of the eye.

10. The device recited in claim 1, further comprising a controller configured to control the mechanism for stopping and starting vibration of the needle.

11. The device recited in claim 1, wherein the port, in combination with the vibrating needle, is configured to liquefy the vitreous by disrupting the integrity of the vitreous using at least one of shear force or viscous heat.

12. A device for removing vitreous from an eye, comprising:

a needle defining a lumen and a port extending to the lumen, the needle being configured for insertion into the vitreous of the eye;

a sample container coupled to the needle and having a chamber in fluid communication with the lumen;

a conduit for fluidly connecting the lumen and the chamber such that the needle and the sample container are longitudinally misaligned from one another;

a vibration mechanism configured to induce vibration of the needle to draw a sample of the vitreous into the port and to the chamber; and a drug delivery system for delivering a therapeutic agent through the port, wherein at least one of the sample container and the drug delivery system extends into the vibration mechanism for reducing an overall length of the device.

13. The device recited in claim 12, wherein the mechanism has a laterally extending passage for receiving an end of the conduit.

14. The device recited in claim 12, wherein the mechanism comprises an ultrasonic transducer having a back mass.

15. The device recited in claim 14, wherein the back mass has a longitudinally extending passage aligned with the needle and receiving an end of the conduit.

16. The device recited in claim 14, wherein the ultrasonic transducer is a langevin transducer.

17. The device recited in claim 14, wherein the ultrasonic transducer operates at a frequency of 20 kHz to 50 KHz.

18. The device recited in claim 14, wherein the ultrasonic transducer energizes piezoelectric crystals to cause an acoustic horn to vibrate.

19. The device recited in claim 12, further comprising a controller configured to control the mechanism for stopping and starting vibration of the needle.

20. The device recited in claim 12, wherein the port, in combination with the vibrating needle, is configured to liquefy the vitreous by disrupting the integrity of the vitreous using at least one of shear force or viscous heat.

21. A method of removing vitreous from an eye, comprising:

providing a needle defining a lumen and a port extending to the lumen, the needle being configured for insertion into the vitreous of the eye;

providing a sample container coupled to the needle and having a chamber in fluid communication with the lumen;

inducing, with a vibration mechanism, vibration of the needle to draw a sample of the vitreous into the port and to the chamber; and delivering, with a drug delivery system, a therapeutic agent through the port, wherein at least one of the sample container and the drug delivery system extends into the vibration mechanism for reducing an overall device length.

* * * * *